United States Patent
Asherman (10) Patent No.: US 7,615,674 B2
(45) Date of Patent: Nov. 10, 2009

(54) BATTLEFIELD CHEST DRESSING

(76) Inventor: Richard Asherman, P.O. Box 222, Wapiti, WY (US) 82450

( * ) Notice: Subject to any disclaimer, the term of this patent is extended or adjusted under 35 U.S.C. 154(b) by 328 days.

(21) Appl. No.: 11/463,829

(22) Filed: Aug. 10, 2006

(65) Prior Publication Data
US 2008/0091152 A1    Apr. 17, 2008

(51) Int. Cl.
- A61F 13/00    (2006.01)
- A61M 1/00     (2006.01)
- A61B 17/00    (2006.01)

(52) U.S. Cl. .................. 602/58; 604/122; 128/887; 128/888

(58) Field of Classification Search .......... 602/41–59; 128/887, 888, 889; 604/304–306, 122; 137/543.15, 137/533.27, 833.21
See application file for complete search history.

(56) References Cited

U.S. PATENT DOCUMENTS

| | | | |
|---|---|---|---|
| 3,522,807 A | 8/1970 | Millenbach | |
| 4,413,621 A | 11/1983 | McCracken et al. | |
| 4,465,062 A | 8/1984 | Versaggi et al. | |
| 4,717,382 A | 1/1988 | Clemens et al. | |
| 5,090,406 A | 2/1992 | Gilman | |
| 5,160,322 A * | 11/1992 | Scheremet et al. | 604/122 |
| 5,195,977 A | 3/1993 | Pollitt | |
| 5,263,922 A | 11/1993 | Sova et al. | |
| 5,431,633 A | 7/1995 | Fury | |
| 5,478,333 A | 12/1995 | Asherman, Jr. | |
| 7,429,687 B2 * | 9/2008 | Kauth et al. | 602/58 |

* cited by examiner

Primary Examiner—Kim M Lewis
(74) Attorney, Agent, or Firm—Merchant & Gould P.C.

(57) ABSTRACT

Embodiments of a chest dressing assembly having a rigid body defining an inner chamber accessible by an opening for placement over a chest wound and one or more protected check valves on the rigid body that allow fluid, e.g., blood or air, to flow out of the chamber but prevent fluid flow into the chamber are disclosed. The body is rigid in order to prevent the dressing from being crushed when heavy clothing such as body armor covers the dressing, or in cold weather climates which require heavy clothing such as Afghanistan. Similarly, the body is shaped and the check valves are located on the body, such as in a recess, in order to prevent the same heavy clothing or body armor from interfering with the operation of the check valves.

12 Claims, 6 Drawing Sheets

BATTLEFIELD CHEST DRESSING

BACKGROUND

When a person is shot, stabbed or injured by shrapnel in the chest, the wound often times penetrates a sufficient distance into the chest cavity to puncture the parietal pleura, visceral pleura, and the lungs. In some cases two wound holes are formed, an entry and an exit hole. A wound hole(s) that penetrates the chest cavity and parietal pleura allows air and/or blood to flow freely into the chest cavity, the pleural space, and possibly the lungs.

The condition wherein air penetrates into the pleural space between the lung and the chest wall through a wound hole in the chest wall is referred to as an open pneumothorax. When an open pneumothorax occurs, the normal mechanism by which the lung expands is lost; i.e., the fluid adhesion of the pleural surface of the lung to the pleural surface of the chest wall. Thus, the affected lung does not expand when the patient inhales and respiratory distress becomes severe and possibly fatal.

For patients with an open wound to the chest, the severity of the open pneumothorax that develops can be minimized by sealing the open wound via an occlusive bandage prior to transport. The occlusive bandage is used to eliminate air penetrating into the pleural space through the wound hole when the patient inhales.

However, if the intake of air into the pleural space is not entirely eliminated, additional air may be trapped in the pleural space, thus causing the pressure in the affected chest cavity to rise, a condition referred to as tension pneumothorax. If the pressure in the chest cavity exceeds normal pressure, blood flow from the heart to the lungs may be halted, with death rapidly following. Thus, it is imperative that when treating an open pneumothorax, that the wound is appropriately sealed in a manner which eliminates air from penetrating into the pleural space through the wound hole.

The current day medical procedures used by first responders to treat an open pneumothorax are occlusive type dressings. For example, (1) petrolatum gauze dressing, (2) a sterilized aluminum foil dressing, or (3) a folded universal dressing placed over the wound. The gauze dressing, foil or universal dressing is taped to the skin on all four sides of the wound. By taping the dressing on all four sides, the first responder is attempting to eliminate air penetrating into the pleural space through the wound.

Yet, in most instances, this type of dressing is ineffective. It either (1) does not totally eliminate air entering the pleural space through the wound; (2) eliminates air penetrating into the pleural space through the wound yet does not allow the already trapped air to escape; or (3) a combination of both. These defects could cause a more serious tension pneumothorax to develop which leads to respiratory insufficiency and heart failure. Consequently, a need exists for a method and apparatus for successfully treating an open pneumothorax that can be used by first responders, which totally eliminates the intake of outside air into the pleural space via the wound hole yet allows already trapped air to escape.

In addition to developing a tension pneumothorax by using defective dressings as discussed above, a patient with an open chest wound and a severe lung laceration may also develop a tension pneumothorax in a different manner. For instance, the bandage may have eliminated air from entering the pleural space through the wound hole, yet if lacerated, the lung will continue to leak air into the pleural space. Consequently, every time the patient inhales, more air becomes trapped in the pleural space, causing more pressure to be exerted on the lacerated lung. This increased pressure on the lacerated lung forces the lung to collapse until reduced to a ball 2-3 inches in diameter. At this point of collapse, pressure in the affected chest cavity begins to rise, the collapsed lung is pressed against the heart and the lung on the opposite side, compressing the remaining uninjured lung. If the pressure in the chest cavity exceeds the normal pressure of the blood returning to the heart, blood flow from the heart to the lungs may be halted, with death rapidly following.

To successfully prevent a tension pneumothorax from developing, the air flow into the pleural space via the wound hole must be eliminated, but the air coming from the lacerated lung must be allowed to escape the pleural space via the wound hole. The method of treatment currently used by first responders is the same type of dressing used to treat an open pneumothorax except it is taped on only three sides of the wound. The untaped side of the bandage theoretically allows air to exit the pleural space through the wound hole when the patient exhales. As the patient inhales, the three sided dressing theoretically collapses against the wound, thus prohibiting air from entering the pleural space through the wound hole.

In most instances, three sided dressings are ineffective. Initially, the amount of blood that normally accompanies the chest wound prohibits the tape from securely attaching the dressing to the patient. Secondly, when the petrolatum gauze dressing is opened, it becomes creased, making it less form fitting to the body. Consequently, air can both enter and exit the chest cavity because the petrolatum gauze is not sucked against the wound when the patient inhales. Petrolatum is also necrotizing to the lung tissue. If petrolatum penetrates the wound and contacts the lung tissue, the lung tissue may die.

In addition to a tension pneumothorax, a patient with a chest wound may also experience a hemothorax. A hemothorax is the presence of blood in the pleural space. The blood in the pleural space may come from lacerated vessels in the chest wall, from lacerated major vessels within the chest cavity itself, or from a lacerated lung. In a hemothorax, the pleural space becomes filled with blood. Normal lung expansion does not occur, and the lung itself is compressed, thus less air is inhaled. In addition, significantly less blood may be available to carry the reduced level of oxygen to the patient's vital organs.

To treat a hemothorax, the blood must be removed from the pleural space to allow the lung to expand to its normal capacity. Current day treatment of a hemothorax by a first responder includes application of an occlusive dressing over the wound, positioning the patient onto the injured side, thus limiting the pooled blood to the wounded side of the chest cavity, immediate ventilatory support, administration of oxygen, and immediate transportation to the hospital. Treatment by first responders does not currently include removal of the accumulated blood from the pleural space. Some type of valved dressing may also be used for hemothorax treatment in this situation, such as the flexible valve dressing described in U.S. Pat. No. 5,478,333.

Finally, first response on the battlefield is complicated by the hostile environment in which it normally occurs. Any treatment must be easy to use and adapted to the rigors of the battlefield environment. For example, medics on the battlefield providing first response often, after placing dressings on a wounded soldier, replace the soldier's chest protecting body armor in order to protect the soldier until such time as the soldier can be removed from the hostile environment. In addition, battlefield transport and conditions often require that the patient be placed on the wounded side. If the patient is suffering from a tension pneumothorax or a hemothorax, these situations have the effect of subjecting the dressing used to external compression and pressure, potentially crushing any delicate portion of the dressing and/or interfering with the dressing's ability to allow trapped fluids to escape, such as in the case of the three-sided dressing and the flexible valve dressing designs discussed above.

SUMMARY

Embodiments of a chest dressing assembly having a rigid body defining an inner chamber accessible by an opening for placement over a chest wound and one or more protected check valves on the rigid body that allow fluid, e.g., blood or air, to flow out of the chamber but prevent fluid flow into the chamber are disclosed. The body is rigid in order to prevent the dressing from being crushed when heavy clothing such as body armor covers the dressing. Similarly, the body is shaped and the check valves are located on the body, such as in a recess, in order to prevent the same heavy clothing or body armor from interfering with the operation of the check valves. This makes the dressing uniquely suited for battlefield use (where body armor is necessary) and for cold weather use (where heavy cold weather clothing is necessary). Multiple valves improve the performance of the dressing by providing redundancy and further allow the dressing to operate effectively throughout a wide range of different affixed angles.

In one aspect, the disclosure describes a medical dressing for treating a patient with a chest wound. The medical dressing includes a three-dimensional rigid body defining an inner chamber accessible via a first opening and at least three check valves disposed on the rigid body. The check valves allow fluid to escape the inner chamber but prevent fluid from entering the inner chamber depending on the relative pressure on each side of the valves (i.e., within the chamber and external to the dressing. In addition, each check valve is located in a different recess in the rigid body thereby protecting the operation of the check valve from interference by clothing or armor worn over the dressing.

In another aspect, the disclosure describes another medical dressing assembly for treating a patient with a chest wound that includes a body formed by a unitary three-dimensional wall having a base circumscribing an opening in the base and the wall enclosing an inner chamber accessible via the opening in the base. The wall includes at least one valve passage therethrough; and at least one fluid release member attached to the wall. The at least one fluid release member allows fluid to escape the inner chamber through the at least one valve passage but prevents fluid from entering the inner chamber through the valve passage. In addition, the three-dimensional wall is shaped so that the at least one fluid release member is operable when the medical dressing is worn between a patient's body and a patient's clothing.

These and various other features as well as advantages will be apparent from a reading of the following detailed description and a review of the associated drawings. Additional features are set forth in the description which follows, and in part will be apparent from the description, or may be learned by practice of the described embodiments. The benefits and features will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments systems and methods described below and are not meant to limit the scope of the invention in any manner, which scope shall be based on the claims appended hereto.

DETAILED DESCRIPTION

A chest dressing assembly is illustrated in the attached drawings. The drawings illustrate a noninvasive chest dressing assembly for preventing pressure build-up in the pleural space of the chest cavity, reducing the possibility of developing a tension pneumothorax from an open pneumothrax or a sucking chest wound, and that allows efficient drainage of a hemothorax.

FIGS. 1-4 illustrate different views of an embodiment of the chest dressing assembly 100 having a rigid body 102 defining an inner chamber 104 accessible by an opening 116 for placement over the wound and one or more protected check valves 106 on the rigid body 102 that allow fluid, e.g., blood or air, to flow out of the chamber 104 but prevent fluid flow into the chamber 104. The body 102 is rigid in order to prevent the dressing from being crushed when heavy clothing such as body armor covers the dressing 100. Similarly, the body 102 is shaped and the check valves 106 are located on the body, such as in a recess, in order to prevent the same heavy clothing or body armor from interfering with the operation of the check valves 106.

In the embodiment shown, the rigid body 102 is dome-shaped, in this case illustrated as hemi-spherically shaped. The body 102 consists of a single piece or wall roughly in the shape of a hemisphere 100 with an attached flange 112 at the base 114 of the hemisphere 110 as shown. Alternative body shapes are possible including cylindrical-, prism-, cube-, cone-, or pyramidal-shaped bodies. In addition, alternative shapes are possible for shape of the base 114 and the opening 116, such as polygonal or elliptical.

The body 102 is three-dimensional and shaped to define an inner chamber 104 that when applied to a patient is exposed to the open chest wound through the opening 116 in the base of the body 102. Because the body 102 is rigid, the inner chamber will not be collapsed by the weight of the clothing or armor worn over the wound after treatment.

In an embodiment, the rigid body 102 is transparent. This allows medical personal to visually inspect the condition of the wound and the circumstances in the inner chamber 104 when the dressing is applied.

The rigid body 102 may be made of any suitably rigid material such as plastic, metal, molded resin, or carbon fiber. In an embodiment, the rigid body is made of a polycarbonate. Polycarbonates are a particular group of thermoplastics that are easily worked, molded, and thermoformed; as such, these plastics are very widely used in modern manufacturing.

In an embodiment, the rigid body 102 is a single unitary piece. The body 102 may be created as separate pieces and then bonded together to form a single, unitary piece or, alternatively initially created as a single piece, such as via an injection molding process.

In the embodiment shown, the rigid body 102 is provided with one or more recessed portions or recesses 120 in order to protect the operation of the valve 106. In addition to recesses 120, other surface features and shapes are also possible such as burrs, overhangs, protective members and different angled surfaces. The recesses 120 are provided to prevent clothing or armor covering the chest dressing 100 from interfering with the operation of the check valve 106. In FIGS. 1-4 an embodiment of the body 102 is shown with three recesses 120, although more or less may be provided as desired (e.g., see FIGS. 5-8). In the embodiment shown, each recess 120 is designed to receive a check valve 106 and includes a portion of the rigid body 102 formed as valve seat 122 adapted to compliment the selected type of check valve 106.

The valve seat 122 includes one or more passages 124 through the rigid body 102 that may be occluded by the check valve 106 depending on the pressure difference at the check valve 106 between the inner chamber 104 and the external environment. Although cylindrically shaped passages 124 are shown, passages 124 may be of any suitable shape and size, as long as the check valve 106 is operable to ensure the one-way flow as described.

The recesses 120 may be cylindrically-shaped having an annular side wall portion and a substantially flat end cap portion that makes up the valve seat 122 as shown as shown in FIGS. 1-4. In the embodiment shown the valve seat 122 includes nearly all of the area of the flat end cap, although this is not necessary. In an alternative embodiment, the recesses 120 may have the shape of a conic section so that the area of the recess 120 at the exterior surface of the rigid body 102 is different (e.g., larger) than the area of the end cap or valve seat 122. Other geometries are also possible including geometries where the side walls of the recesses 120 are based on the shape of a sphere, pyramid, prism, cube or some other shape.

FIGS. 1-4 illustrate an embodiment of the chest dressing provided with check valves 106 in the form of an umbrella valve 106. Check valves are mechanical valves that permit gases and liquids to flow in only one direction, preventing process flow from reversing. An umbrella valve is one type of check valve that may adapted for use in the chest dressing. Other types of check valves that may also be used include duckbill valves, umbrella valves, cross slit valves, ball-check valves, cone-check valves, and a swing valves.

Depending on the type of check valve 106 used, the rigid body 102 is provided with a complimentary valve seat 122 adapted to work with the selected check valve 106. In addition, the type of check valve 106 selected may also dictate the acceptable shapes of the recess 120 and potentially obviate the need for a recess altogether.

For example, in the embodiment shown, the valve seat 122 is a substantially flat portion within the recess 120 adapted to compliment the umbrella valve 106 shown. The valve seat 122 includes six passages 124 through the body 102 for the flow of fluids. In addition, the valve seat 122 is provided with a seventh hole for the stem 130 of the umbrella valve 106.

In the embodiment shown, the umbrella valve 106 (referring now to FIG. 8 and FIG. 3) includes a circular flap 136 provided with a central stem 130 that includes a barrel 134 and a retention barb 132. In an embodiment, the umbrella vale 106 is made of a flexible material suitable for sterilization and medical device use such as the silicone elastomer vinyl-methyl-silicone rubber (also known as "VMQ"). Other suitable materials potentially include elastomers of fluorosilicone, fluorocarbon, nitrile, ethylene, propylene, natural rubber, thermoplastic elastomers, and butyl.

Figure 1:
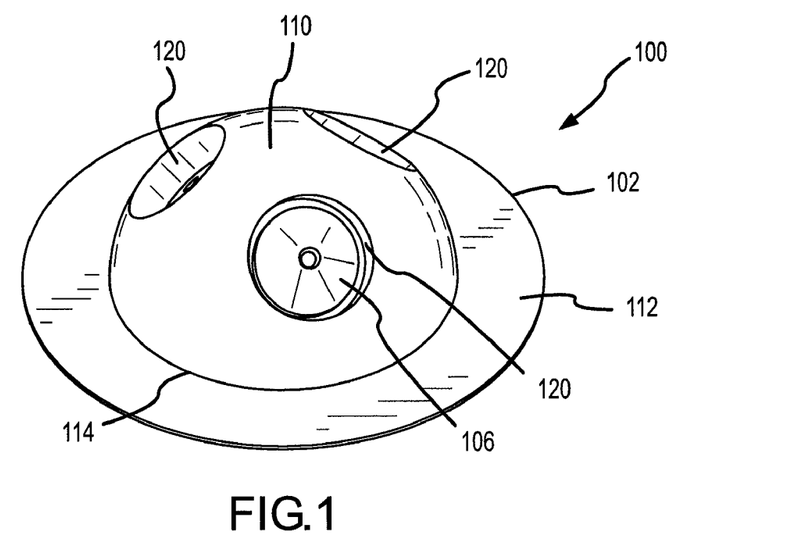
FIG. 1 is a perspective view of the top surface a three-valve embodiment of the medical chest dressing.
Figure 2:
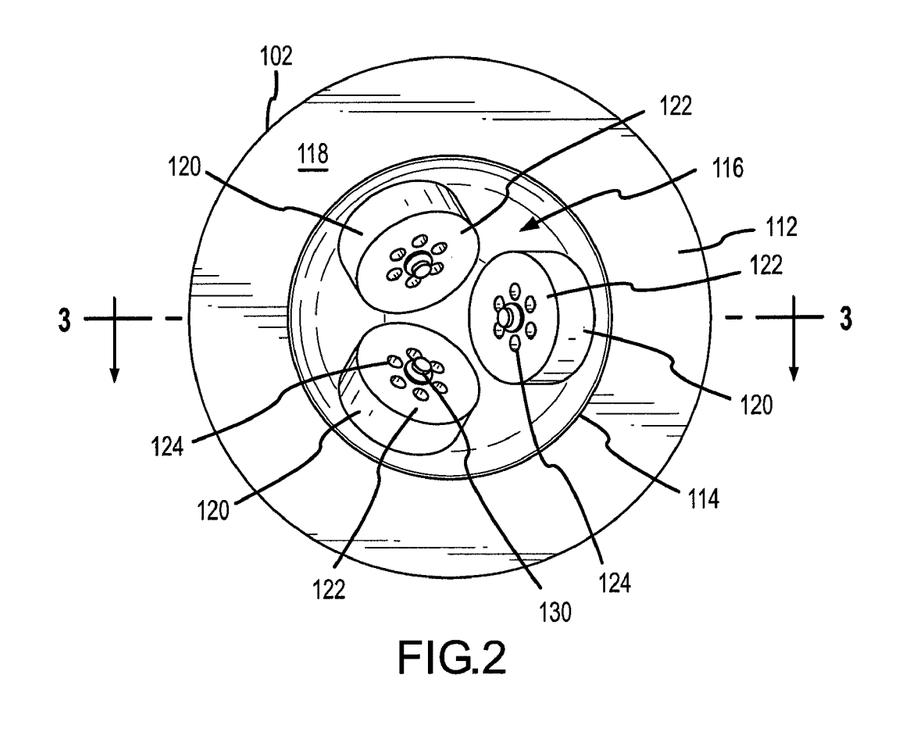
FIG. 2 is a plan view of the chest wound side of the three-valve embodiment of the medical chest dressing shown in FIG. 1.
Figure 3:
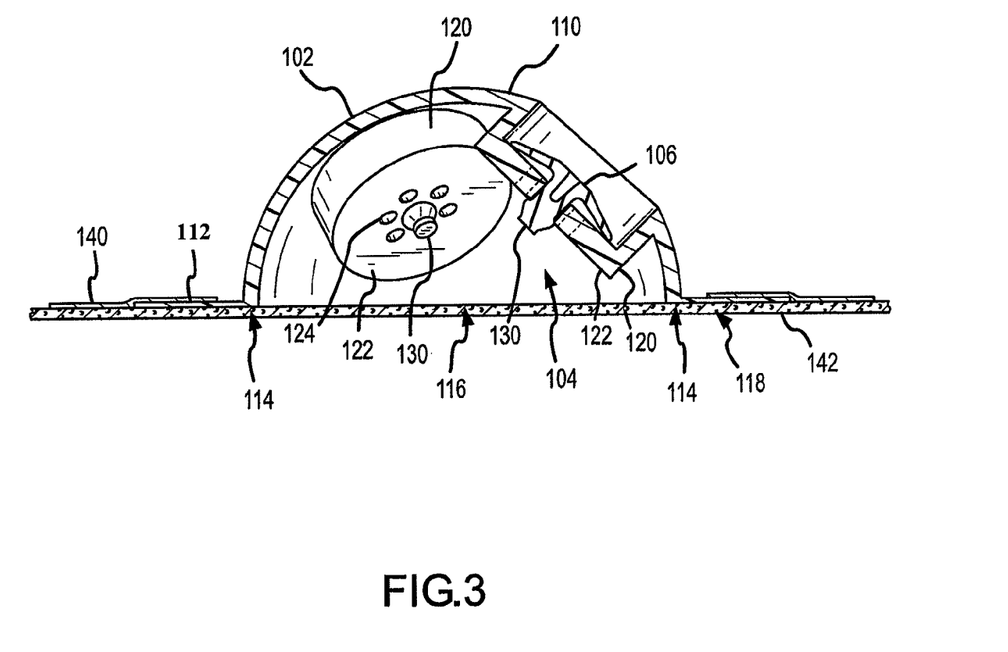
FIG. 3 is a cross-sectional view of an embodiment of the medical chest dressing FIG. 1 attached to a body attachment means.
Figure 4:
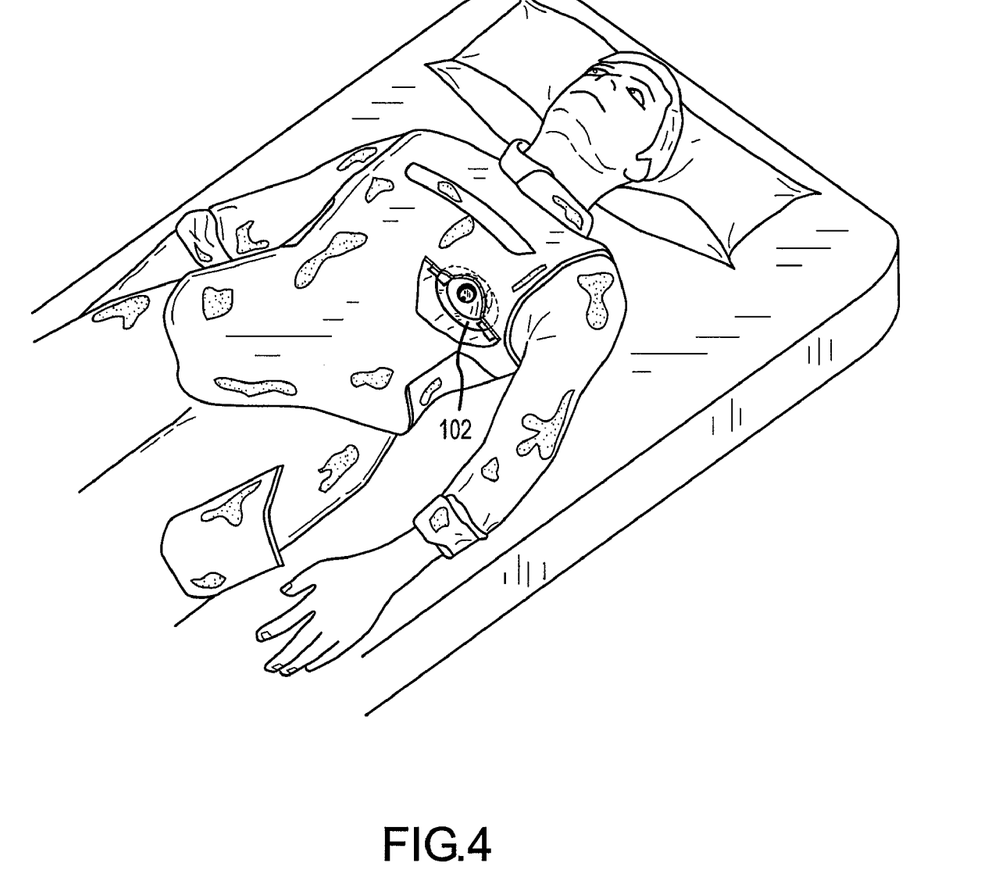
FIG. 4 illustrates the chest dressing affixed to patient wearing protective body armor.
Figure 8:
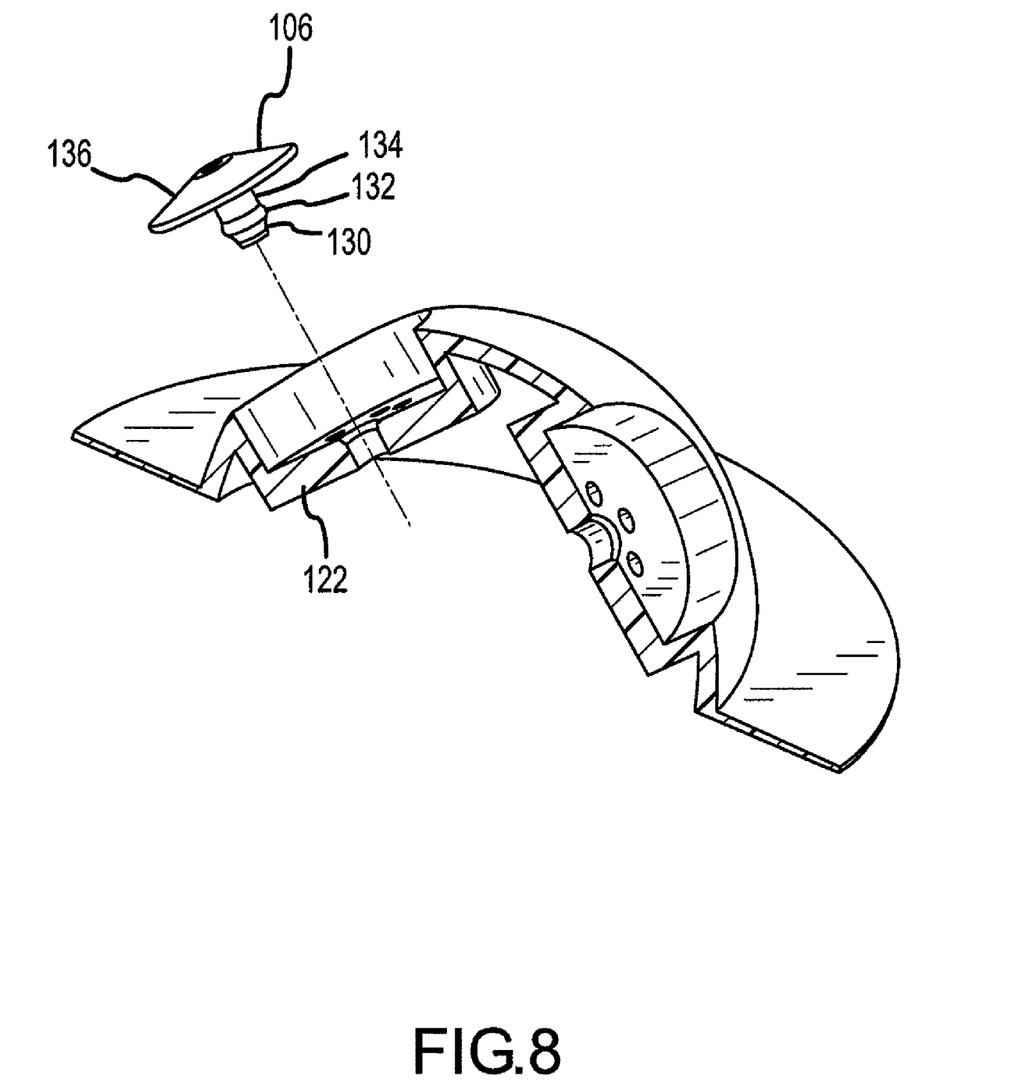
FIG. 8 is a cut-away view illustrating the parts of an umbrella valve embodiment of the chest dressing.

The umbrella valve 106 is installed in the rigid body 102 by inserting the barb 132 completely through the seventh hole so that the barb retains the valve 106 in place. The flexibility of the flap then provides the static force necessary to block the flow passages in the valve seat 122 when the pressure at the inner chamber side of the valve 106 and the pressure at the other side of the valve, i.e., the external side of the dressing exposed to the environment, are the same. As described above, the umbrella valve 106 acts as a check valve to allow fluid, e.g., blood or air, to flow out of the inner chamber 104 (when the pressure at the inner chamber side of the valve 106 is greater than the pressure at the other side of the valve) but prevent fluid flow into the chamber (when the pressure at the inner chamber side of the valve 106 is less than the pressure at the other side of the valve).

In an embodiment, the chest dressing 100 is further provided with a means to attach the rigid body to the skin or body of the patient. The attachment means may be as simple as adhesive provided on the patient-side 118 of the flange 114.

In the embodiment shown in FIG. 3, the attachment means 140 is a sheet 140 of flexible material such as a flexible polymeric material capable of being sterilized. The sheet 140 may be of any suitable shape and provided with a hole sized to allow the dome 110, but not all of the flange 114 of the rigid body 102 to be inserted. The sheet 140 may be further provided with adhesive that then attaches the sheet 140 to the flange 114 of the rigid body 102. Suitable adhesives include non-air permeable hypo-allergenic adhesives such as Product No. 1524 by 3M. Alternative ways of attaching a sheet 140 to the body 102 are also possible including thermal bonding depending on the materials selected for the body 102 and the sheet 140.

For transportation and storage, the assembly 100 may be further provided with a tear-away backing to protect the adhesive. The tear away backing 142 is removed to expose the adhesive surface of the sheet 140 so that the dressing 100 may be placed onto a wound. The adhesive surface of the sheet 140 may be same adhesive surface that connects the sheet 140 to the body 102.

Alternative means for attaching the body 102 to the patient are also possible and known in the art including, for example, adjustable bandages designed to encompass the patient's body. Any suitable attachment means may be used as desired.

Figure 5:
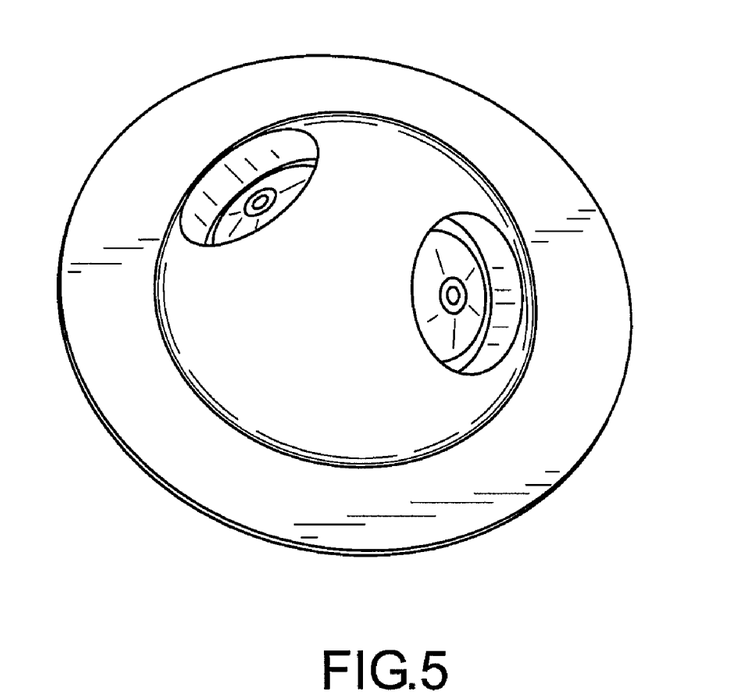
FIG. 5 is a perspective view of a two-valve embodiment of the chest dressing.
Figure 6:
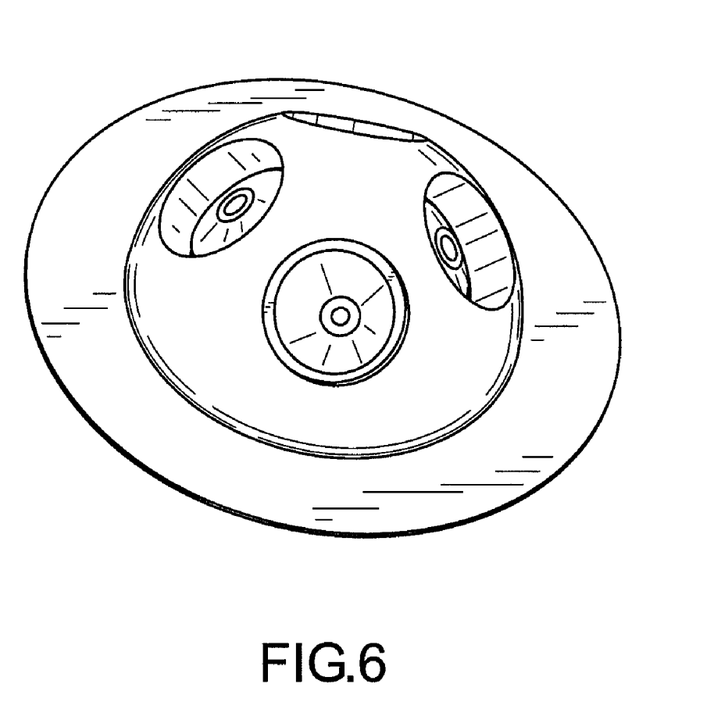
FIG. 6 is a perspective view of a four-valve embodiment of the chest dressing.
Figure 7:
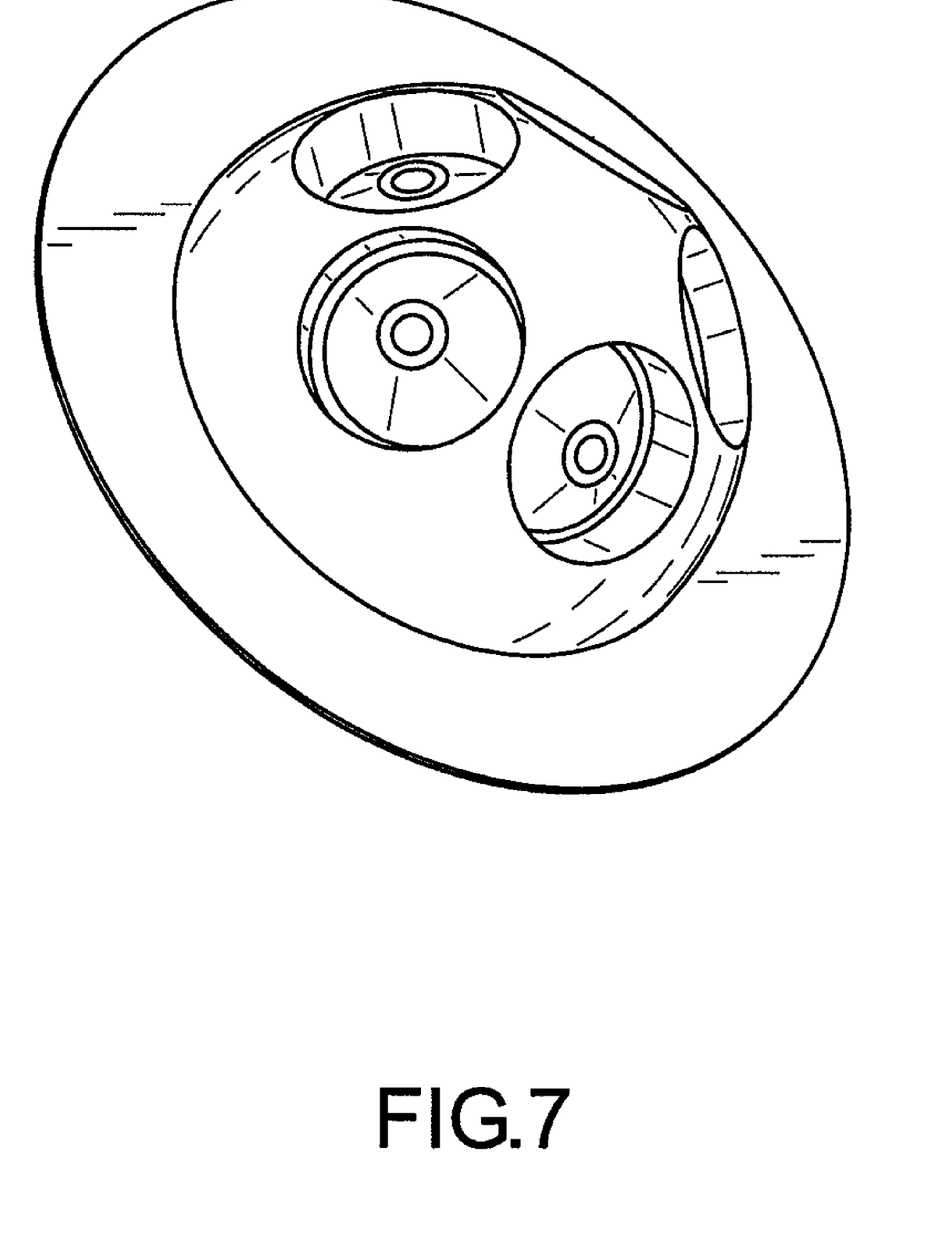
FIG. 7 is a perspective view of a five-valve embodiment of the chest dressing.

FIGS. 5-7 illustrate alternative embodiments of the chest dressing in which two, four or five check valves are provided. The benefit of having multiple check valves at different locations in the dressing include redundancy of check valves. In addition, regardless of the angle of the dressing on the patient and the angle of repose of the patient, multiple check valves also allow blood and other liquids to drain from the dressing without requiring that the inner chamber be completely filled with fluid first.

Those skilled in the art will recognize that the methods and systems of the present disclosure may be implemented in many manners and as such are not to be limited by the foregoing exemplary embodiments and examples. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad valve, body shape and attachment means combinations are possible in achieving the functions, features, interfaces and preferences described herein. Moreover, the scope of the present disclosure covers conventionally known manners for carrying out the described features and functions and interfaces, and those variations and modifications that may be made to the components described herein as would be understood by those skilled in the art now and hereafter.

While various embodiments have been described for purposes of this disclosure, various changes and modifications may be made which are well within the scope of the present invention. For example, a pyramidal embodiment may be utilized with a different valve type on each face of the pyramid body. In addition, one or more of the valves may be replaced by an access port or a two way check valve such as a combination duckbill/umbrella valve to allow medicine to be easily applied to the wound without the need to remove the dressing. Numerous other changes may be made which will readily suggest themselves to those skilled in the art and which are encompassed in the spirit of the invention disclosed and as defined in the appended claims.

What is claimed is:

1. A medical dressing for treating a patient with a chest wound comprising:
    a three-dimensional rigid body defining an inner chamber accessible via a first opening; and
    at least two check valves disposed on the rigid body, the check valves allowing fluid that has entered via the first opening to escape the inner chamber but preventing fluid from entering the inner chamber via the check valves; wherein each check valve is located in a different recess in the rigid body.

2. The medical dressing of claim 1 further comprising: a means for attaching the rigid body over the chest wound.

3. The medical dressing of claim 2 wherein the means for attaching includes a flexible material attached to the rigid body, the flexible material provided with adhesive for attaching to a patient's body near the chest wound.

4. The medical dressing of claim 3 wherein the rigid body is provided with a flange that is adhesively attached to the flexible material.

5. The medical dressing of claim 1 wherein the rigid body is transparent and made of polycarbonate.

6. The medical dressing of claim 1 wherein the rigid body is dome shaped.

7. The medical dressing of claim 1 wherein the check valves are umbrella valves.

8. The medical dressing of claim 7 wherein each umbrella valve comprises:
    a flap in its associated recess of the rigid body and adjacent to a valve seat portion of the rigid body, the valves seat portion including one or more second openings through the rigid body to the inner chamber; and wherein the flap is adapted to move between a first position occluding the one or more second openings so that fluid cannot flow into the inner chamber through the one or more second openings; and
    a second position that permits flow of fluid out of the inner chamber through the one or more second openings.

9. The medical dressing of claim 1 wherein the check valves are selected from duckbill valves, umbrella valves, cross slit valves, ball-check valves, cone-check valves, and a swing valves.

10. A medical dressing assembly for treating a patient with a chest wound comprising:
    a body formed by a unitary three-dimensional wall having a base circumscribing an opening in the base and the wall enclosing an inner chamber accessible via the opening in the base, the wall having at least one valve passage therethrough;
    at least one fluid release member attached to the wall, the at least one fluid release member operable to allow fluid to escape the inner chamber through the at least one valve passage but preventing fluid from entering the inner chamber through the valve passage; and wherein the three-dimensional wall is shaped so that the at least one fluid release member is operable when the medical dressing is worn between a patient's body and a patient's clothing; and
    two fluid release members attached to the wall.

11. A medical dressing assembly for treating a patient with a chest wound comprising:
    a body formed by a unitary three-dimensional wall having a base circumscribing an opening in the base and the wall enclosing an inner chamber accessible via the opening in the base, the wall having at least one valve passage therethrough;
    at least one fluid release member attached to the wall, the at least one fluid release member operable to allow fluid to escape the inner chamber through the at least one valve passage but preventing fluid from entering the inner chamber through the valve passage; and wherein the three-dimensional wall is shaped so that the at least one fluid release member is operable when the medical dressing is worn between a patient's body and a patient's clothing; and
    wherein there are three fluid release members attached to the wall.

12. A medical dressing assembly for treating a patient with a chest wound comprising:
    a body formed by a unitary three-dimensional wall having a base circumscribing an opening in the base and the wall enclosing an inner chamber accessible via the opening in the base, the wall having at least one valve passage therethrough;
    at least one fluid release member attached to the wall, the at least one fluid release member operable to allow fluid to escape the inner chamber through the at least one valve passage but preventing fluid from entering the inner chamber through the valve passage; and wherein the three-dimensional wall is shaped so that the at least one fluid release member is operable when the medical dressing is worn between a patient's body and a patient's clothing; and
    wherein there are more than three fluid release members attached to the wall.

* * * * *